United States Patent
Ousdigian et al.

(10) Patent No.: US 6,438,407 B1
(45) Date of Patent: Aug. 20, 2002

(54) METHOD AND APPARATUS FOR MONITORING PHYSIOLOGIC PARAMETERS CONJUNCTION WITH A TREATMENT

(75) Inventors: Kevin T. Ousdigian, St. Paul; Karen A. Stone, White Bear Lake; Vasant Padmanabhan, Maple Grove, all of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/528,627

(22) Filed: Mar. 20, 2000

(51) Int. Cl.$^7$ .................................................. A61B 5/04

(52) U.S. Cl. ........................................................ 600/510

(58) Field of Search ................................. 600/510, 523, 600/513; 607/5

(56) References Cited

U.S. PATENT DOCUMENTS

| | | |
|---|---|---|
| 4,223,678 A | 9/1980 | Langer et al. |
| 4,295,474 A | 10/1981 | Fischell |
| 4,428,378 A | 1/1984 | Anderson et al. |
| 4,561,442 A | 12/1985 | Vollmann et al. |
| 4,903,701 A | 2/1990 | Moore et al. |
| 4,941,471 A | 7/1990 | Mehra |
| 5,081,988 A | 1/1992 | Cook et al. |
| 5,088,488 A | 2/1992 | Markowitz et al. |
| 5,107,833 A | 4/1992 | Barsness |
| 5,135,004 A | 8/1992 | Adams et al. |
| 5,168,871 A | 12/1992 | Grevious |
| 5,292,343 A | 3/1994 | Blanchette et al. |
| 5,309,919 A | 5/1994 | Snell et al. |
| 5,312,446 A | 5/1994 | Holschbach et al. |
| 5,314,450 A | 5/1994 | Thompson |
| 5,324,315 A | 6/1994 | Grevious |
| 5,330,513 A | 7/1994 | Nichols et al. |
| 5,331,966 A | 7/1994 | Bennett et al. |
| 5,354,319 A | 10/1994 | Wyborney et al. |
| 5,383,909 A | 1/1995 | Keimel |
| 5,411,031 A | 5/1995 | Yomtov |
| 5,433,736 A | 7/1995 | Nilsson |
| 5,437,285 A | 8/1995 | Verrier et al. |

(List continued on next page.)

*Primary Examiner*—Scott M. Getzow
(74) *Attorney, Agent, or Firm*—Girma Wolde-Michael

(57) ABSTRACT

A system including an implantable medical device and an associated external device, in which the implantable device is adapted to monitor a physiologic parameter and includes a telemetry system for transmitting information to and receiving information from the external device, including information regarding the measured physiological parameter and in which wherein the external device includes a telemetry system for receiving information from the implanted device and for transmitting information to the implanted device and is provided with a mechanism for receiving information indicative of occurrences of significant therapeutic events and is further provided with a display system which combines information received from the implantable device related to the monitored physiologic parameter with the information of therapeutic significance and for displays the combined information in a time-scaled display in which the measured physiologic parameter is displayed along a common time scale with indications of occurrences of the significant therapy related events. The implantable device may also include a mechanism for delivering a therapy; and the mechanism in the external device for receiving information indicative of occurrences of significant therapeutic events may receive information regarding changes in the therapy delivered by the implantable device. The mechanism in the external device for receiving information indicative of occurrences of significant therapeutic events may also or in addition receive information indicative of changes in the therapy delivered by a physician, e.g. changes in a drug therapy.

8 Claims, 11 Drawing Sheets

U.S. PATENT DOCUMENTS

| | | |
|---|---|---|
| 5,466,245 A | 11/1995 | Spinelli et al. |
| 5,487,755 A | 1/1996 | Snell et al. |
| 5,497,780 A | 3/1996 | Zehender |
| 5,513,645 A | 5/1996 | Jacobson et al. |
| 5,540,232 A * | 7/1996 | Laney et al. |
| 5,545,186 A | 8/1996 | Olson et al. |
| 5,564,434 A | 10/1996 | Halperin et al. |
| 5,603,331 A | 2/1997 | Heemels et al. |
| 5,669,391 A | 9/1997 | Williams |
| 5,722,999 A | 3/1998 | Snell |
| 5,749,900 A | 5/1998 | Schroeppel et al. |
| 5,752,976 A | 5/1998 | Duffin et al. |
| 5,755,736 A | 5/1998 | Gillberg et al. |
| 5,785,660 A | 7/1998 | van Lake et al. |
| 5,814,085 A | 9/1998 | Hill |
| 5,824,029 A | 10/1998 | Weijand et al. |
| 5,893,882 A | 4/1999 | Peterson et al. |
| 5,951,485 A * | 9/1999 | Cyrus et al. |
| 6,045,513 A | 4/2000 | Stone et al. |

* cited by examiner

METHOD AND APPARATUS FOR MONITORING PHYSIOLOGIC PARAMETERS CONJUNCTION WITH A TREATMENT

BACKGROUND OF THE INVENTION

The present invention relates generally to implantable medical devices and more particularly to implantable medical devices intended for use in monitoring a patient's heart rhythm or other physiologic parameters.

Implantable pacemakers and cardioverters monitor the heart's rhythm in order to detect arrhythmias and deliver appropriate therapies to terminate detected arrhythmias. In conjunction with this function, the ability of the device to store information with regard to monitored heart rhythms has dramatically increased over the past two years. Examples of implantable pacemakers and defibrillators which have the capability of storing information related to monitored heart rhythms include U.S. Pat. No. 4,223,678 issued to Langer et al., U.S. Pat. No. 5,722,999 issued to Snell, U.S. Pat. No. 5,513,645 issued to Jacobsen et al. and U.S. Pat. No. 5,312,446 issued to Holschbach et al. In addition, there have recently been developed implantable monitoring devices that do not deliver any anti-arrhythmia therapies to the heart but simply store information regarding a patient's heart rhythms for later uplink to an external device. Such devices are disclosed in U.S. Pat. No. 5,331,966 issued to Bennett et al., U.S. Pat. No. 5,135,004 issued to Adams and U.S. Pat. No. 5,497,780 issued to Zehender.

In conjunction with implantable devices as described above, information stored relating to a patient's heart rhythm may include information relating to heart rate trends over time, as disclosed in U.S. Pat. No. 5,088,488 issued to Markowitz et al., U.S. Pat. No. 5,330,513 issued to Nichols et al. and U.S. Pat. No. 5,603,331 issued to Heemels et al. as well as information relating to heart rate variability over time, as disclosed in U.S. Pat. No. 5,749,900 issued to Schroeppel et al., U.S. Pat. No. 5,466,245 issued to Spinelli et al., U.S. Pat. No. 5,411,131 issued to Yomtov et al. and U.S. Pat. No. 5,437,285 issued to Verrier et al. Other information relating to heart rhythms may also be stored, particularly in conjunction with occurrences of cardiac arrhythmias. Storage of such information, along with information relating to the patient's condition or treatment is disclosed in U.S. Pat. No. 4,561,442, issued to Vollmann, U.S. Pat. No. 5,722,999, issued to Snell and U.S. Pat. No. 4,295,474, issued to Fischell, all incorporated herein by reference in their entireties.

In addition to storing information relating to heart rhythms, implantable devices may also store information regarding outputs of physiologic sensors such as activity sensors, respiration sensors and the like. For example, storage of sensor output trends is disclosed in U.S. Pat. No. 5,088,488 by Ledin et al. Storage of long term trends of heart rates and activity sensor or other physiologic sensor output is disclosed in the above-cited commonly assigned U.S. patent application Ser. No. 09/078,221, filed May 13, 1998 by Stone et al., for an "Implantable Medical Device for Tracking Patient Functional Status", U.S. patent application Ser. No. 09/452,659, filed Dec. 1, 1998 by Padmanabhan et al., for a "Method and Apparatus for Monitoring Heart Rate" and U.S. patent application Ser. No. 09/452,452,533, filed Dec. 1, 1999 by Padmanabhan et al., for a "Method and Apparatus for Monitoring Heart Rate", both incorporated herein by reference in their entireties

SUMMARY OF THE INVENTION

The present invention is directed toward an implantable device having enhanced capabilities for monitoring a patient's condition and/or the patient's response to therapies provided by the implanted device over extended periods of time, e.g. time periods of over a months, preferably time periods extending over several months. The implanted device, in conjunction with an associated external monitor or programmer provides a mechanism displaying these monitored parameters in conjunction with simultaneous time-based display of significant events associated with an ongoing treatment regimen. Preferably, monitored physiologic parameters and information indicative of the patient's response to delivered therapies are displayed in the form of trend lines, histograms or scatter plots illustrating values of the measured parameters on one axis and time on another axis. Multiple physiologic parameters are preferably simultaneously displayed on the same time scale. Events associated with an ongoing treatment regimen are simultaneously displayed, arranged along a time axis corresponding to the time axes of the displayed physiologic parameter trend lines. Displayed events preferably include significant occurrences associated with the ongoing therapy, such as initiation of the therapy, termination of therapy, changes in the therapy and other changes in the patient's condition or lifestyle. By displaying the monitored parameters in concurrent with and along the same time scale as the significant therapeutic events, the effectiveness of therapies delivered by the device and/or by the patient's physician over time may be determined and adjustments to the therapy may more easily be evaluated.

In the context of a therapy delivered by an implantable pacemaker, for example, the therapies may include anti-bradycardia cardiac pacing, anti-tachycardia cardiac pacing, and tachyarrhythmia prevention cardiac pacing or pacing for treatment of heart failure. In conjunction with such devices, the significant events to be displayed may include initiation of a pacing mode, changes of pacing mode, changes in electrode configurations or changes in pacing parameters within a pacing mode, such as rate response adjustments, lower pacing rates changes, and activation or deactivation of optional features within a pacing mode, such as rate-variable refractory periods or A-V intervals, rate smoothing, or the like. In the context of an implantable anti-tachyarrhythmia device, significant events to be displayed might include delivery of, enablement of or changes in the therapies provided, e.g. anti-tachycardia pacing therapies and high voltage therapies, as well as changes in the detection criteria for triggering the therapies. In the context of an implantable drug dispenser, such events might include initiation of delivery of a drug, changes in the drug delivered and modification of the timing or dosage of the delivered drug. Correspondingly, changes in the operational parameters of implantable nerve or muscle stimulators, implantable apnea stimulators or the like may also be monitored.

Physiologic parameters to be monitored may include the types of parameters presently monitored by implantable devices such as pacemakers, defibrillators, implanted monitors and the like, such as heart rate, heart rate variability, patient activity levels, hemodynamic parameters, respiration, blood oxygen levels, ST segment elevation or depression, occurrences of tacharrhythmias, QRS or ST segment morphology and the like. In conjunction with the display of detected tachyarrhythmias, information relating to the rates of the detected tachyarrhythmias and/or the detection criteria then in effect for the tachyarrhythmias may also be displayed. As implanted chemical sensors are further refined, for example in conjunction with implantable drug pumps, monitored parameters may include blood glucose level, electrolyte levels, metabolite levels or other chemical parameters of diagnostic interest with respect to the drug regimen provided by the device. Monitored parameters indicative of the effect of the therapy provided by the implanted device may include numbers and timing of delivered therapies and effectiveness of delivered therapies. Similar parameters to those discussed above may also be monitored by implanted monitoring devices which themselves do not deliver a therapy, and may also be displayed along with significant events associated with therapies provided by other means, such as orally delivered drug regimens, dietary regimens, surgical procedures or the like.

In some embodiments of the invention, all information to be displayed, including the monitored parameters and the therapy related events are stored in the implantable device. In other embodiments, the displayed information may be stored partly in the implantable device and partly in conjunction with an external programmer or monitor. In still other embodiments, all displayed information may be permanently stored in the external programmer or monitors. In embodiments of all three types, it is envisioned that in general, at least some physiologic parameters to be displayed are acquired by the implantable device and transmitted by telemetry to the associated external programmer or monitor. Display of the information may be accomplished by means of a CRT or LCD type display and/or by means of a paper print-out.

DETAILED DESCRIPTION OF THE PREFERRED EMBODIMENTS

Figure 1:
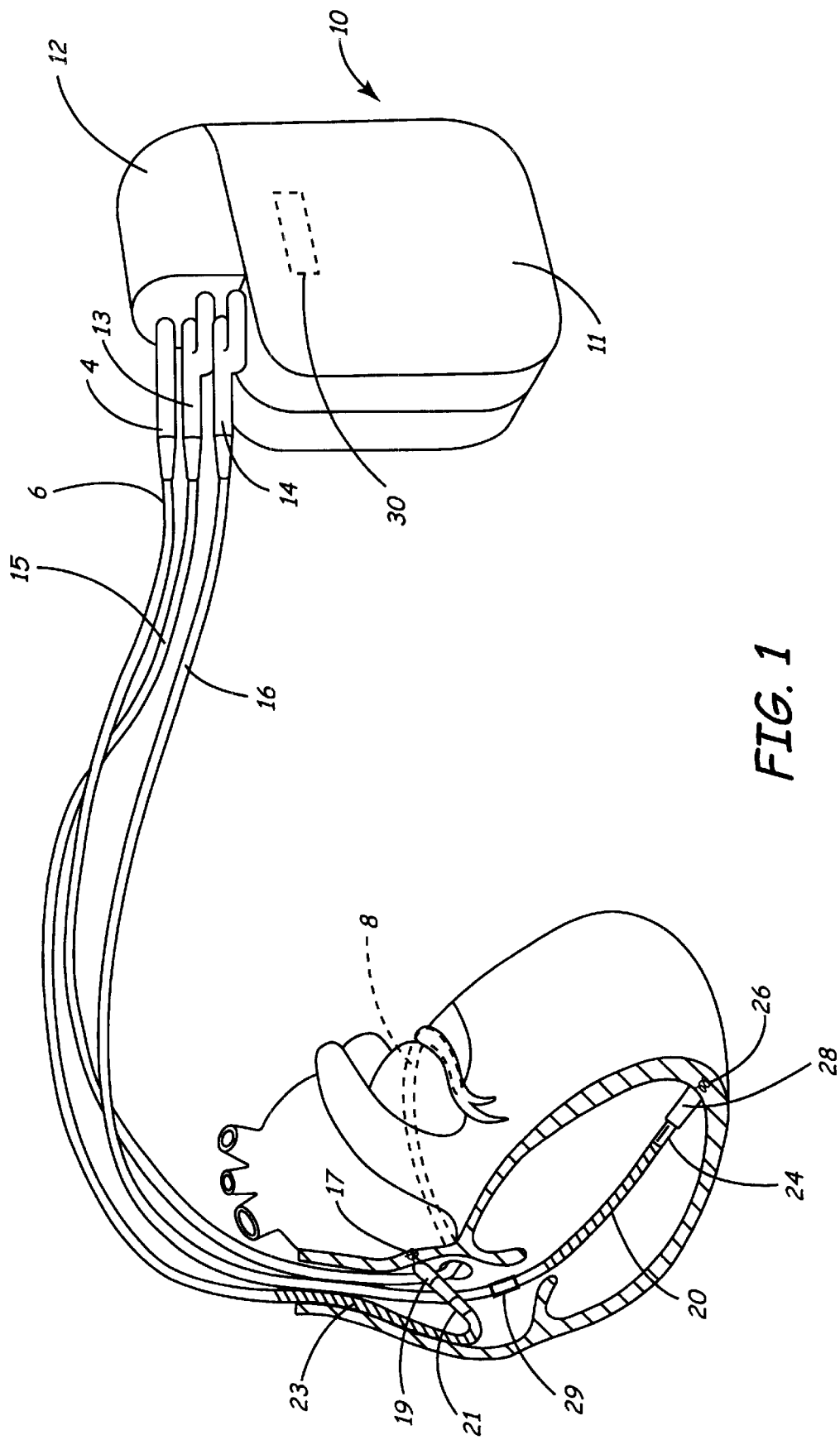
FIG. 1 illustrates an implantable pacemaker/cardioverter/defibrillator of a type useful in practicing the present invention, in conjunction with a human heart.

FIG. 1 illustrates an exemplary implantable defibrillator and lead set of a type in which the present invention may usefully be practiced. The ventricular lead includes an elongated insulative lead body 16, carrying three mutually insulated conductors. Located adjacent the distal end of the lead are a ring electrode 24, an extendable helix electrode 26, mounted retractably within an insulative electrode head 28, and an elongated coil electrode 20. Each of the electrodes is coupled to one of the conductors within the lead body 16. Electrodes 24 and 26 are employed for cardiac pacing and for sensing ventricular depolarizations. The sensed ventricular depolarizations may be employed to produce a long-term record of heart rate trends as described in the above-cited Padmanabhan et al application. At the proximal end of the lead is a bifurcated connector 14 that carries three electrical connectors, each coupled to one of the coiled conductors.

The atrial/SVC lead includes an elongated insulative lead body 15, also carrying three mutually insulated conductors. Located adjacent the J-shaped distal end of the lead are a ring electrode 21 and an extendible helix electrode 17, mounted retractably within an insulative electrode head 19. Each of the electrodes is coupled to one of the conductors within the lead body 15. Electrodes 17 and 21 are employed for atrial pacing and for sensing atrial depolarizations. An elongated coil electrode 23 is provided, proximal to electrode 21 and coupled to the third conductor within the lead body 15. At the proximal end of the lead is a bifurcated connector 13 that carries three electrical connectors, each coupled to one of the coiled conductors.

The coronary sinus lead includes an elongated insulative lead body 6, carrying one conductor, coupled to an elongated coiled defibrillation electrode 8. Electrode 8, illustrated in broken outline, is located within the coronary sinus and great vein of the heart. At the proximal end of the lead is a connector plug 4, which carries an electrical connector, coupled to the coiled conductor.

The pacemaker/cardioverter/defibrillator 10 includes a hermetic enclosure 11 containing the electronic circuitry used for generating cardiac pacing pulses for delivering cardioversion and defibrillation shocks and for monitoring the patient's heart rhythm. Pacemaker/cardioverter/defibrillator 10 is shown with the lead connector assemblies 4, 13 and 14 inserted into the connector block 12, which serves as a receptacle and electrical connector for receiving the connectors, 4, 13 and 14 and interconnecting the leads to the circuitry within enclosure 11. An activity sensor 30 is illustrated schematically by broken outline, and may be an accelerometer or a piezoelectric transducer. Sensor 30 may be used for monitoring patient activity levels in conjunction with the present invention, for later display and analysis, for example as described in the above-cited Stone et al. application. Activity sensor 126 may be used as well as for regulation of pacing rate based upon demand for cardiac output. An optional additional or alternative physiologic sensor 29 which may take the form of an oxygen sensor, pressure sensor, temperature sensor, impedance sensor of any of the various types employed for monitoring demand for cardiac output or for measuring heart hemodynamics is shown positioned on lead body 16. Sensor 124 may be used in conjunction with or as an alternative to the activity sensor 30 in conjunction with measurement of long-term physiologic parameter trends according to the present invention.

Figure 2:
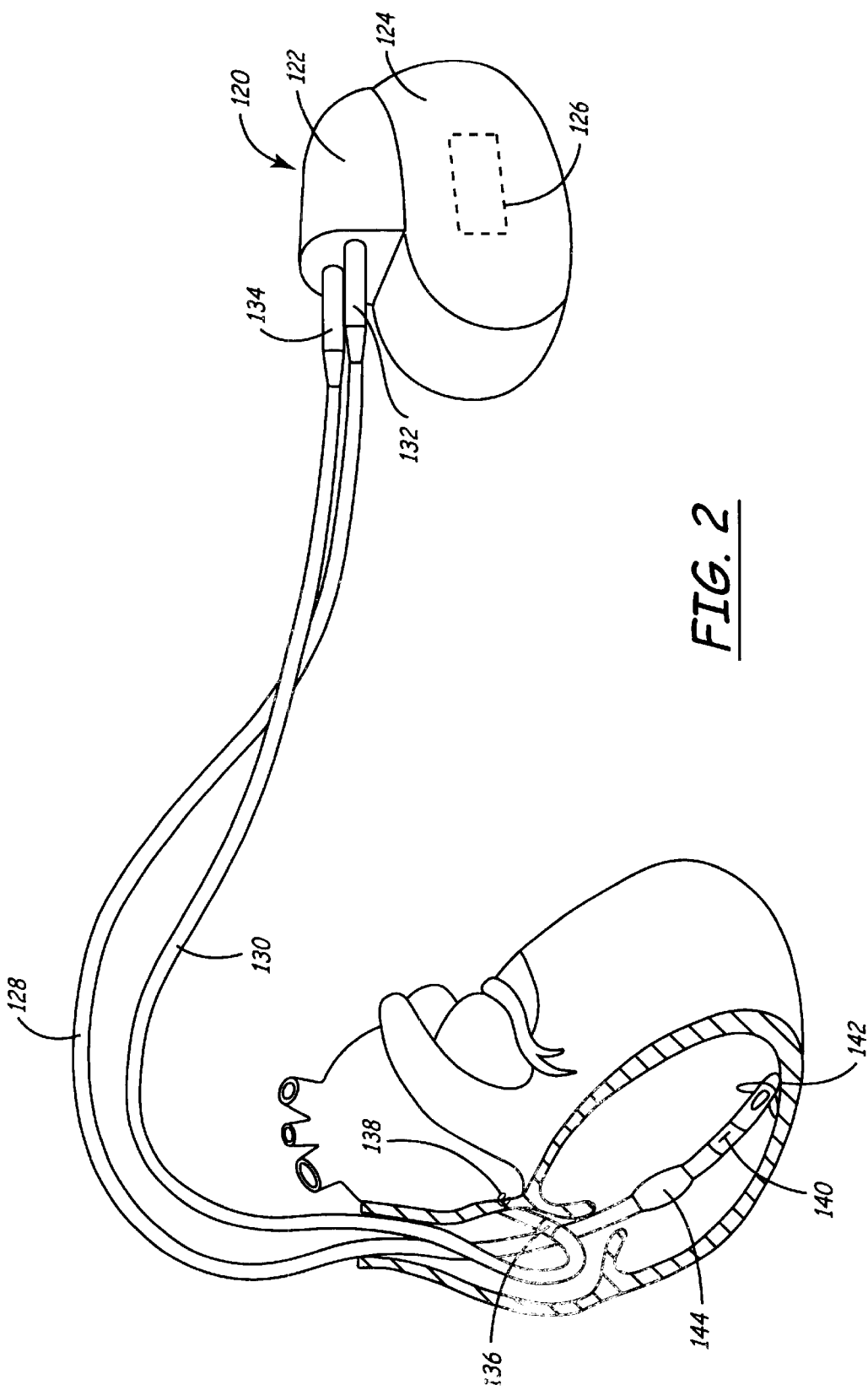
FIG. 2 illustrates an implantable pacemaker of a type useful in practicing the present invention, in conjunction with a human heart.

FIG. 2 illustrates a cardiac pacemaker of a type appropriate for use in practicing the present invention in conjunction with its associated lead system, illustrated in relation to a patient's heart. The pacemaker 120 includes a hermetic enclosure 124 containing the electronic circuitry used for generating cardiac pacing pulses and for monitoring the patient's heart rhythm. An activity sensor 126 is illustrated schematically by broken outline, and may be an accelerometer or a piezoelectric transducer as discussed above in conjunction with FIG. 1. Mounted to the enclosure 124 is a header 122 which serves as a receptacle and electrical connector for receiving the connectors 132 and 134 of pacing leads 128 and 130 and interconnecting the leads to the circuitry within enclosure 124. Lead 128 is a ventricular lead provided with electrodes 140 and 142 for monitoring right ventricular heart signals. Also illustrated on lead 128 is a physiologic sensor 144 which may optionally be included in addition to or as an alternative to the activity sensor 126, and which may take the form of an oxygen sensor, pressure sensor, temperature sensor, impedance sensor or any of the various types employed for monitoring demand for cardiac output or for measuring heart hemodynamics. Sensor 124 may be used in conjunction with or as an alternative to the activity sensor 126 for measurement of long-term physiologic parameter trends according to the present invention. Atrial lead 130 carries electrodes 136 and 138 and is employed for sensing and pacing the patient's atrium.

Figure 3:
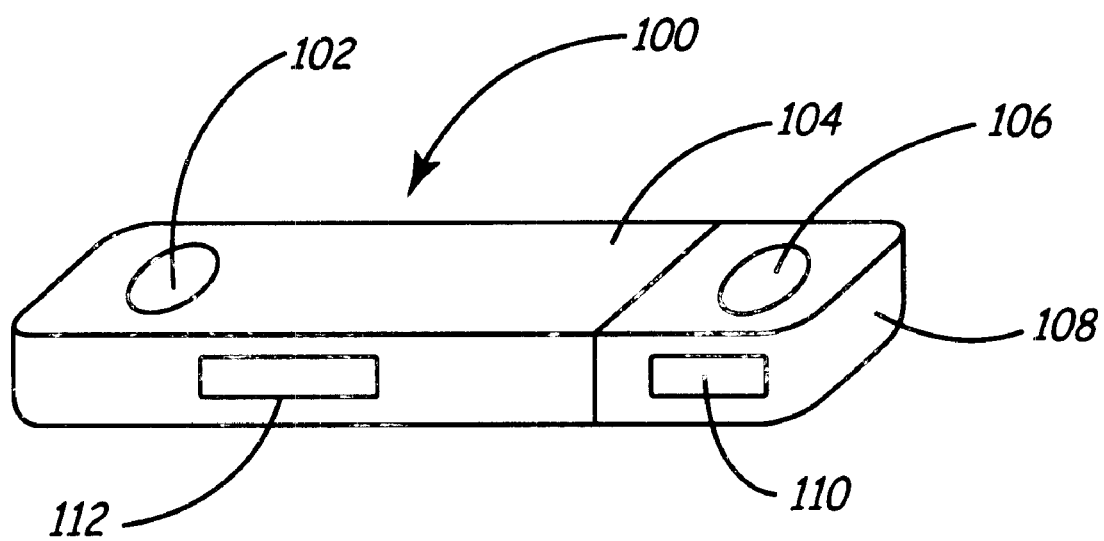
FIG. 3 illustrates an implantable monitor of a type useful in practicing the present invention.

FIG. 3 illustrates a subcutaneously implantable monitor of a type appropriate for use in practicing the present invention. The monitor shares the external configuration of the Medtronic Reveal® implantable monitor, and is provided with a hermetically sealed enclosure 104 containing the electronic circuitry used for generating cardiac pacing pulses and for monitoring the patient's heart rhythm and which carries a molded plastic header 108. The enclosure 104 and the header 108 each carry an electrode 102 and 106, respectively for monitoring heart rhythm. Also mounted in the header 108 is an antenna 110 for use in communicating between the device and an external programmer. Illustrated in broken outline at 112 is an internal activity sensor, of the type typically employed in the context of rate responsive cardiac pacemakers, taking the form either of an accelerometer or a piezo-electric transducer. Other sensors as discussed might also be added to the device, located either on the device enclosure 104 or on an electrical lead extending from the enclosure, for location of the sensor in a desired location subcutaneously or in the vasculature. For example, an absolute pressure sensor or dP/dt type pressure sensor might be located on a right ventricular lead.

Figure 4:
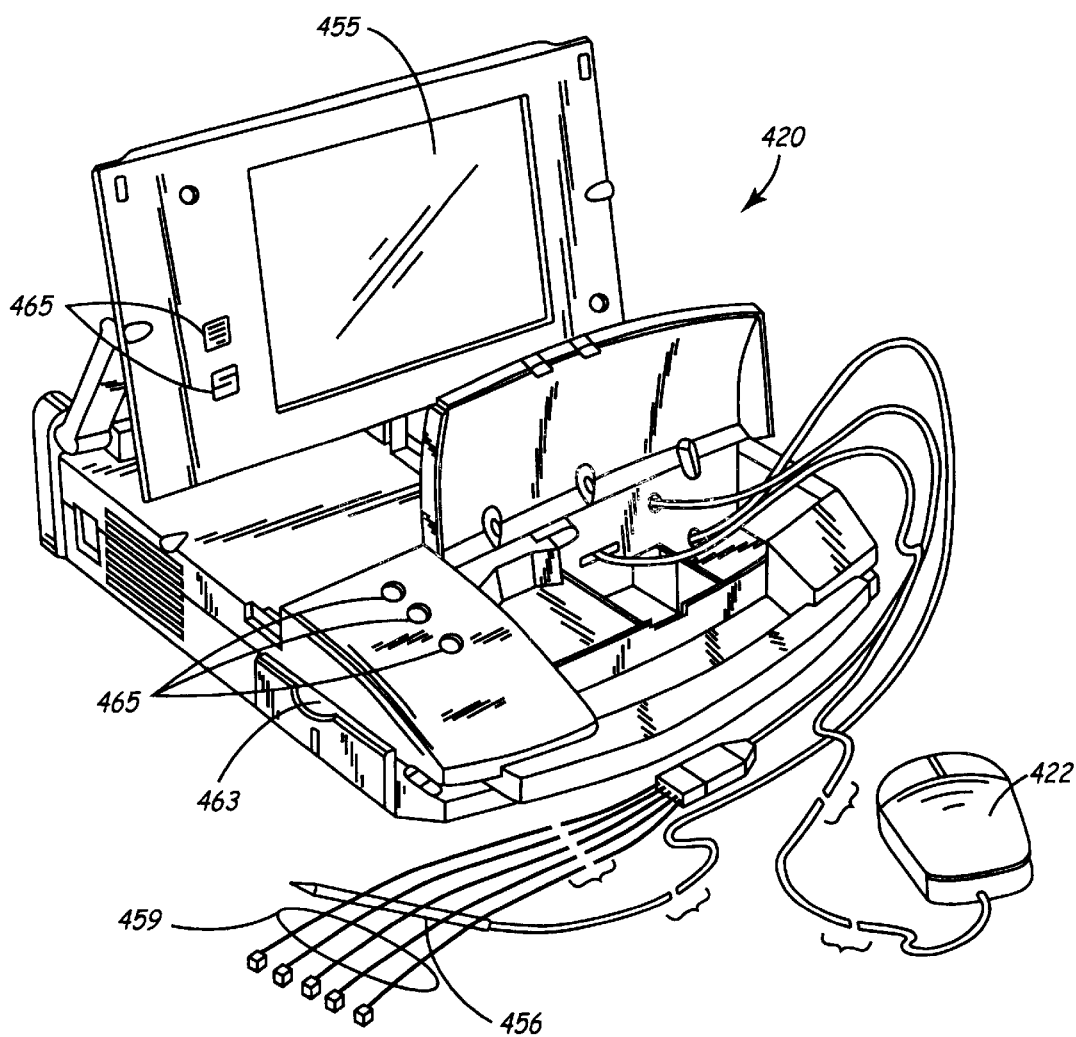
FIG. 4 is a perspective view of a programmer of a type useful in practicing the present invention.

FIG. 4 is a plan view of an external programmer of a sort appropriate for use in the practice of the present invention in conjunction with any of the devices of FIGS. 1–3. The programmer 420 is a microprocessor controlled device which is provided with a programming head 422 for communicating with an implanted device, a set of surface electrogram electrodes 459 for monitoring a patient's electrogram, a display 455 which is preferably a touch sensitive display, control buttons or keys 465, and a stylus 456 for use in conjunction with the touch sensitive screen 455. By means of the control keys 465 and the touch sensitive screen 455 and stylus 456, the physician may format commands for transmission to the implantable device. By means of the screen 455, the physician may observe information telemetered from the implantable device. The programmer is further provided with a printer 463 which allows for hard copy records of displays of signals received from the implanted device such as electrograms, stored parameters, programmed parameters and information as to heart rate trends according to the present invention. While not visible in this view, the device may also be provided with a floppy disk or CD ROM drive and/or a port for insertion of expansion cards such as P-ROM cartridges, to allow for software upgrades and modifications to the programmer 420.

In the context of the present invention, programmer 420 may serve simply as a display device, displaying up-linked information with regard to physiologic parameter trends and with regard to therapy related events, e.g. pacing mode/parameter changes, stored by the associated implantable device. The programmer 420 may also or alternatively receive information by keyboard entry, stylus entry or by other means related to therapy related events, e.g. a change in an oral drug regimen, performance of a surgical procedure such as cardiac ablation, or the like, the programmer storing these entries along with associated time codes for later display. The programmer 420 may also or alternatively store information related to programming of the implanted device by the programmer, to define the therapy delivered by the device. Similarly, as an alternative to long term storage of monitored physiologic parameters by the implantable device, the programmer 420 may employ uplinked information related to shorter term monitoring periods or real time monitoring by the implanted device and may construct long term trend records from these shorter term records, for example as described in the above cited Sell patent. These long-term trend records may be stored in the programmer 20 or, as in the Snell patent, may be down linked for storage in the implanted device.

Figure 5:
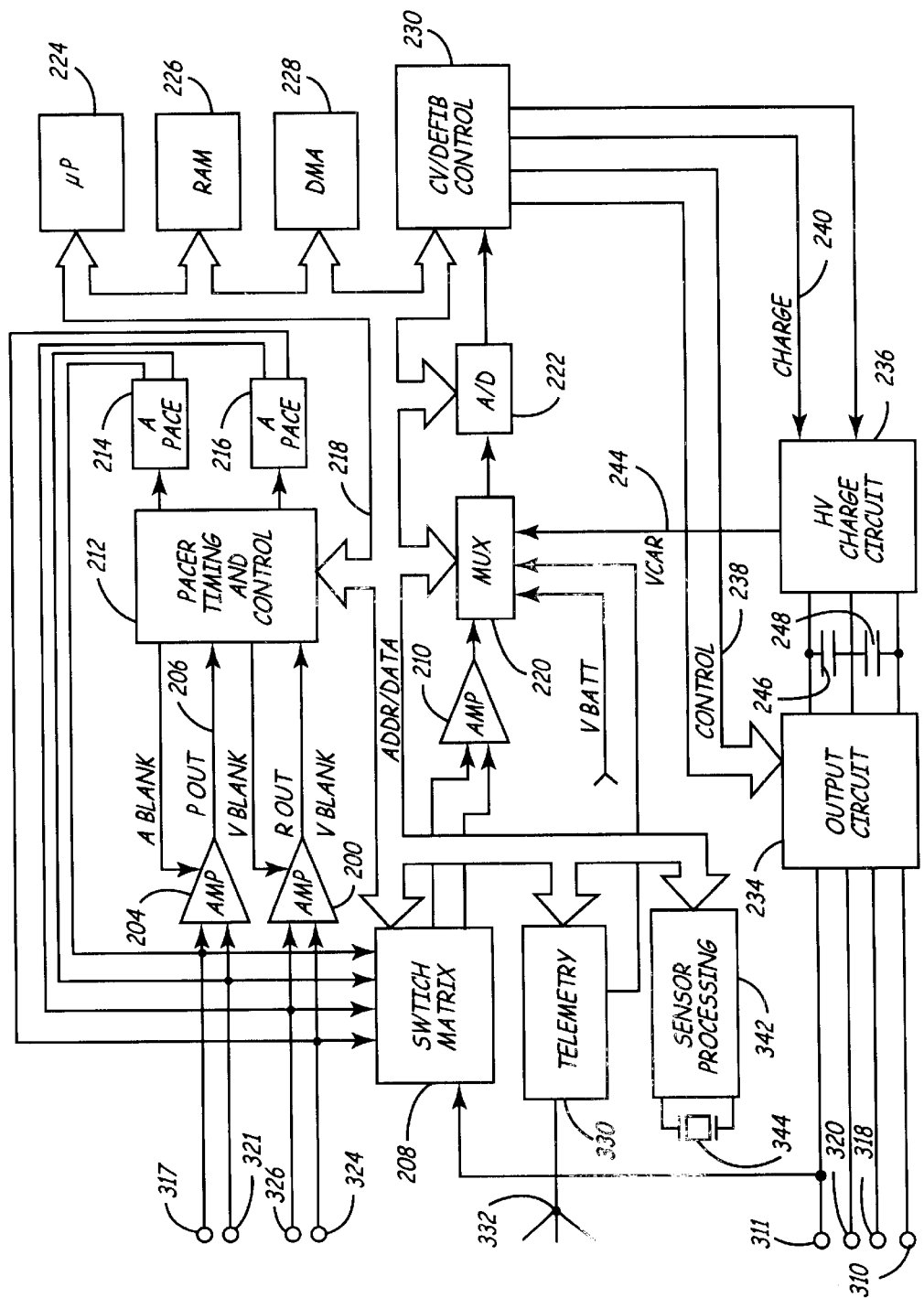
FIG. 5 is a functional schematic diagram of an implantable pacemaker/cardioverter/defibrillator of a type useful in practicing the present invention.

FIG. 5 is a functional schematic diagram of an implantable pacemaker/cardioverter/defibrillator of the type illustrated in FIG. 3, in which the present invention may usefully be practiced. This diagram should be taken as exemplary of one type of anti-tachyarrhythmia device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to electrode 11, and is the uninsulated portion of the housing of the implantable pacemaker/cardioverter/defibrallator. Electrode 320 corresponds to electrode 20 and is a defibrillation electrode located in the right ventricle. Electrode 310 corresponds to electrode 8 and is a defibrillation electrode located in the coronary sinus. Electrode 318 corresponds to electrode 28 and is a defibrillation electrode located in the superior vena cava. Electrodes 324 and 326 correspond to electrodes 24 and 26, and are used for sensing and pacing in the ventricle. Electrodes 317 and 321 correspond to electrodes 19 and 21 and are used for pacing and sensing in the atrium.

Electrodes 310, 311, 318 and 320 are coupled to high voltage output circuit 234. Electrodes 324 and 326 are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are coupled to the P-wave amplifier 204, which preferably also takes the form of an automatic gain controlled amplifier providing an adjustable sensing threshold as a function of the measured R-wave amplitude. A signal is generated on P-out line 206 whenever the signal sensed between electrodes 317 and 321 exceeds the present sensing threshold. Any of the numerous prior art sense amplifiers employed in implantable cardiac pacemakers, defibrillators and monitors may also usefully be employed in conjunction with the present invention.

Switch matrix 208 is used to select which of the available electrodes are coupled to wide band amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal-processing methodologies known to the art.

Telemetry circuit 330 receives downlink telemetry from and sends uplink telemetry to the by means of antenna 332. Data to be uplinked to an associated programmer or monitor and control signals for the telemetry circuit are provided by microprocessor 224 via address/data bus 218. Received telemetry from the associated programmer or monitor is provided to microprocessor 224 via multiplexer 220. The atrial and ventricular sense amp circuits 200, 204 produce atrial and ventricular EGM signals, which also may be digitized, and uplink telemetered to an associated programmer on receipt of a suitable interrogation command. The particular telemetry system employed is not critical to practicing the invention, and any of the numerous types of telemetry systems known for use in implantable devices may be used. In particular, the telemetry systems as disclosed in U.S. Pat. No. 5,292,343 issued to Blanchette et al., U.S. Pat. No. 5,314,450, issued to Thompson, U.S. Pat. No. 5,354,319, issued to Wyborny et al. U.S. Pat. No. 5,383,909, issued to Keimel, U.S. Pat. No. 5,168,871, issued to Grevious, U.S. Pat. No. 5,107,833 issued to Barsness or U.S. Pat. No. 5,324,315, issued to Grevious, all incorporated herein by reference in their entireties, are suitable for use in conjunction with the present invention. However, the telemetry systems disclosed in the various other patents cited herein which are directed to programmable implanted devices, or similar systems may also be substituted. The telemetry circuit 330 is of course also employed for communication to and from an external programmer, as is conventional in implantable anti-arrhythmia devices.

The device of FIG. 5 may additionally be provided with an activity sensor and/or other sensor 344. If sensor 344 is an activity sensor, it may be mounted to the interior surface of the device housing or to the hybrid circuit within the device housing. The sensor 344 and sensor present in circuitry 342 may be employed in the conventional fashion described in U.S. Pat. 4,428,378 issued to Anderson et al, incorporated herein by reference in its entirety, to regulate the underlying pacing rate of the device in rate responsive pacing. In addition, the sensor 344 may be employed to track the functional status of the patient as in the above-cited application by Stone et al. In such case, the device may also store trend information with regard to the number of and/or durations of periods in which the patient's physical activity meets or exceeds a defined level. As noted above, other sensor types may be employed as substitutes or in addition to an activity sensor. Such sensors may include, for example, pressure sensors as in U.S. Pat. No. 5,564,434 issued to Halperin et al., oxygen saturation sensors as described in U.S. Pat. No. 5,903,701 issued to Moore, impedance sensors as disclosed in U.S. Pat. No. 5,824,029 issued to Weijand et al., or temperature sensors as disclosed in U.S. Pat. No. 5,081,988, issued to Cook, et al., all incorporated by reference in their entireties. Sensor-processing circuitry 342 may correspond to the associated sensor processing circuitry as disclosed in the above-cited patents. Information from these sensors may be employed as described below to construct long-term trend records in conjunction with the present invention.

The remainder of the circuitry is dedicated to the provision of cardiac pacing, cardioversion and defibrillation therapies, and, for purposes of the present invention may correspond to circuitry known in the prior art. An exemplary apparatus is disclosed for accomplishing pacing, cardioversion and defibrillation functions as follows. The pacer timing/control circuitry 212 includes programmable digital counters which control the basic time intervals associated with DDD, VVI, DVI, VDD, AAI, DDI, DDDR, VVIR, DVIR, VDDR, AAIR, DDIR and other modes of single and dual chamber pacing well known to the art. Circuitry 212 also controls escape intervals associated with anti-tachyarrhythmia pacing in both the atrium and the ventricle, employing, any anti-tachyarrhythmia pacing therapies known to the art.

Intervals defined by pacing circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to the pacing circuitry 212 via address/data bus 218. Pacer circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on time-out trigger generation of pacing pulses by pacer output circuits 214 and 216, which are coupled to electrodes 317, 321, 324 and 326. The escape interval counters are also reset on generation of pacing pulses, and thereby control the basic timing of cardiac pacing functions, including anti-tachyarrhythmia pacing.

The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, PR intervals and R-P intervals, which measurements are stored in memory 226 and are used in conjunction with the present invention to measure heart rate variability and heart rate trends and in conjunction with tachyarrhythmia detection functions.

Microprocessor 224 operates as an interrupt driven device, and is responsive to interrupts from pacer timing/control circuitry 212 corresponding to the occurrences of sensed P-waves and R-waves and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts. Microprocessor 224 includes associated ROM in which the stored program controlling its operation as described below resides. A portion of the memory 226 (FIG. 2) may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The arrhythmia detection method of the present invention may include any of the numerous available prior art tachyarrhythmia detection algorithms. One preferred embodiment may employ all or a subset of the rule-based detection methods described in U.S. Pat. No. 5,545,186 issued to Olson et al., U.S. Pat. No. 5,755,736 issued to Gillberg et al., all incorporated herein by reference in their entireties. However, any of the various other arrhythmia detection methodologies known to the art might also be employed.

In the event that an atrial or ventricular tachyarrhythmia is detected, and an anti-tachyarrhythmia pacing regimen is desired, timing intervals for controlling generation of anti-tachyarrhythmia pacing therapies are loaded from microprocessor 224 into the pacer timing and control circuitry 212, to control the operation of the escape interval counters therein and to define refractory periods during which detection of R-waves and P-waves is ineffective to restart the escape interval counters.

In the event that generation of a cardioversion or defibrillation pulse is required, microprocessor 224 employs the escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization. In the illustrated device, delivery of the cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse.

In conjunction with the present invention, information from the sensor or sensors, the sense amplifiers and the arrhythmia detection and arrhythmia treatment functions may be stored by microprocessor 224 in RAM 226. Information stored may, for example, include trend information related to heart rates, sensor outputs and tachyarrhythmia detections, as described in the above-cited Stone et al. patent. Trend records may also be stored relating to operational characteristics of the implanted device, such as battery voltage, electrode impedance, sensing and pacing thresholds and the like. Additional information may include information related to the number and timing of anti-arrhythmia therapies delivered, success of delivered anti-arrhythmia therapies and the like, as in currently available implantable defibrillators. As noted above, these trend records may be stored in either or both of the implanted device and the associated programmer or monitor.

In addition to information related to the patient's physiological condition and the operation of the device, the microprocessor 224 may also store time-stamped information in RAM 226 related to therapeutically significant events, as discussed above. For example, in conjunction with a change in a patient's drug regimen, the physician may enter information indicative of the date and nature of the changes by means of the associated programmer or monitor. This information may be stored in the programmer or monitor in conjunction with other information regarding the patient and the implanted device and/or may be down linked to the implanted device for long-term storage in RAM 226. In simpler embodiments, the implanted device and/or programmer may simply store an indication that a drug therapy change was made, without indicating the specific nature of the change. Information regarding surgical procedures, such as ablations, or other heart surgery may be similarly stored. On reprogramming of the implantable device, the implanted device and/or programmer may similarly store time stamped information relating to the nature of the programming change or simply indicating that a change has been made. As discussed below, the time stamped information with regard to significant events is displayed by the associated programmer or monitor along with the trend lines relating to the patient's physiologic condition in a fashion, which simplifies the determination of the effects the events, have with respect to the patient's health.

Figure 6:
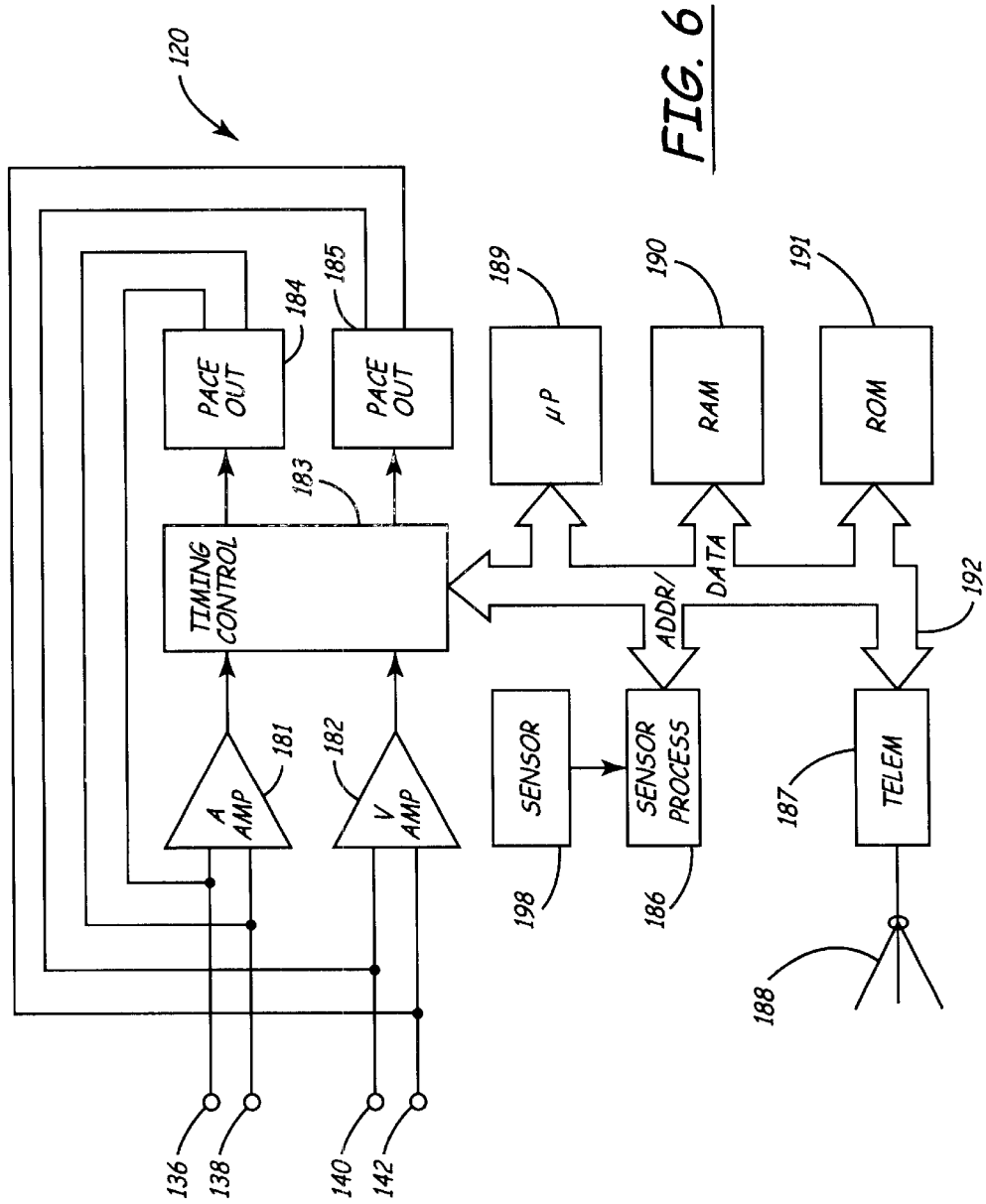
FIG. 6 is a functional schematic diagram of an implantable pacemaker of a type useful in practicing the present invention.

FIG. 6 is a functional schematic diagram of the pacemaker 120 illustrated in FIG. 2. The pacemaker of FIGS. 2 and 6 is essentially a set of subcomponents of the implantable pacemaker/cardioverter/defibrillator illustrated in FIGS. 1 and 5. Like the device of FIG. 5, the pacemaker is a microprocessor-controlled device with microprocessor 189 operating under control of programming stored in Read Only Memory (ROM) 191. In the device as illustrated, electrodes 136 and 138, intended for location in the atrium of the patient's heart are coupled to an atrial amplifier 181 which may correspond to atrial amplifier 204 in FIG. 5. Similarly, ventricular electrodes 140 and 142 are coupled to ventricular amplifier 182, which may correspond to ventricular amplifier 200 in FIG. 5. The outputs of atrial and ventricular amplifiers 181 and 182 are input into timing and control circuitry 183 which conforms generally to the pacer timing and control circuitry 212 of FIG. 5, and which measures intervals between detected depolarizations and controls intervals between delivered pacing pulses as well as generating interrupts via data/address 192 to awake microprocessor 189 in response to delivery of a pacing pulse or sensing of a cardiac depolarization. Intervals between depolarizations measured by timing/control circuitry 183 are stored in Random Access Memory (RAM) 190 until processed by microprocessor 189 to derive average heart rate values. Atrial and ventricular pacing pulses delivered according to one or more of the standard pacing modes described in conjunction with FIG. 5 are produced by atrial and ventricular pulse generator circuits 184 and 185 which may correspond to pulse generator circuits 215 ad 216 in FIG. 5.

The sensor 198 illustrated in FIG. 6 may correspond to sensor 344 as described in conjunction with FIG. 5 and may be an activity sensor or any of the above described alternative or additional sensors. Sensor processing circuitry 186 may correspond to sensor processing circuitry 342, as described in conjunction with FIG. 5. In the context of the present invention, the sensor 198 is employed to for purposes of controlling the gathering and storage of information related to long-term heart rate trends. Sensor 198 may also be employed to proved rate responsive pacing and/or for use in conjunction with detection of arrhythmias. Telemetry circuitry 187 in conjunction with antenna 188 serves to transmit information to and receive information from an external programmer precisely as described above in conjunction with the device of FIG. 5, including information stored in RAM 190 related to the functioning of the device, the physiologic condition of the patient and/or significant therapy-related events.

Figure 7:
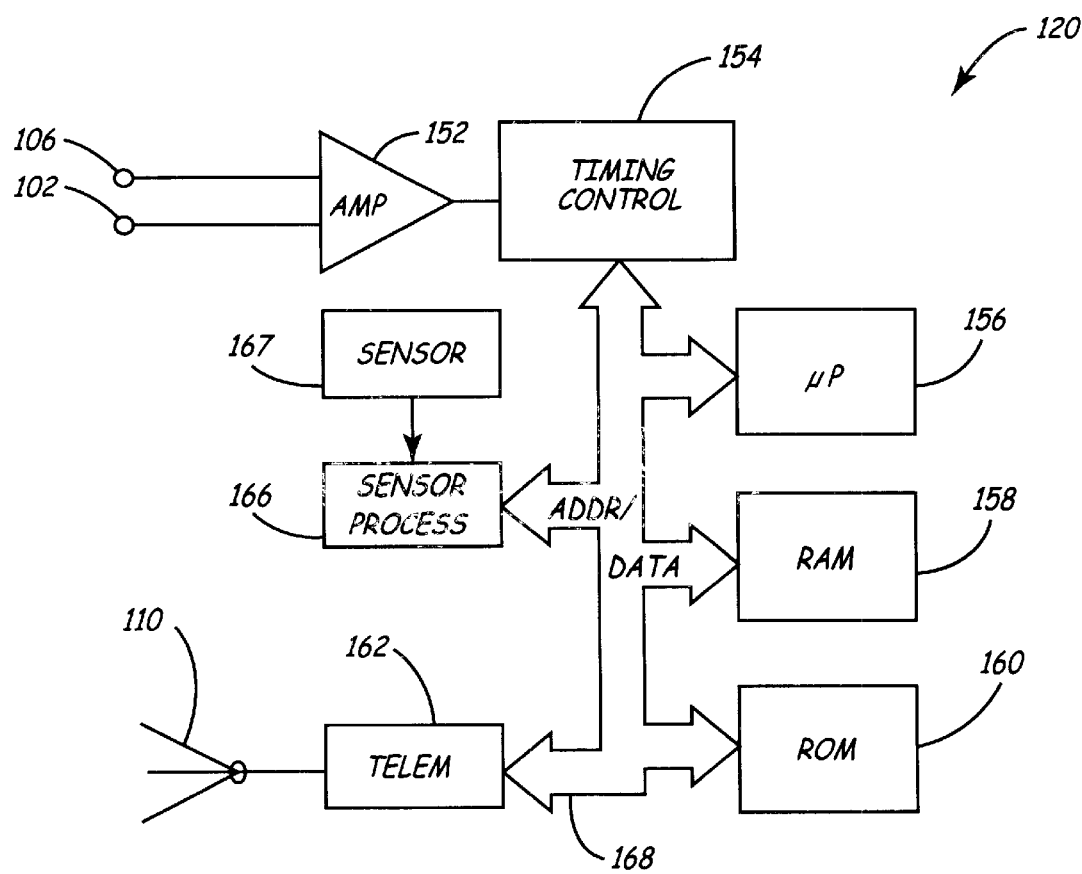
FIG. 7 is a functional schematic diagram of an implantable monitor of a type useful in practicing the present invention.

FIG. 7 illustrates the functional organization of the subcutaneously implantable heart monitor 100 illustrated in FIG. 3. This device consists essentially of a set of subcomponents of the more complex embodiment of the invention disclosed in FIG. 5, and includes a sense amplifier 152 coupled to electrodes 102 and 106, illustrated in FIG. 1. Sense amplifier 152 may correspond to sense amplifier 204 or 200 in FIG. 5. Like the device of FIG. 5, the implantable monitor may be a microprocessor control device operating under control microprocessor 156 with its functionality controlled primarily by software stored in the read only memory associated therein. In this context, amplifier 152 detects the occurrence of heart depolarizations, with timing/control circuitry 154 serving to measure the durations between the detected heart depolarizations and to generate interrupts awakening microprocessor 156 so that it may store, analyze and process the detected intervals. Random Access Memory (RAM) 158 serves to store information related to the functioning of the device, the physiologic condition of the patient and/or significant therapy-related events. Like the device in FIG. 5, timing and control circuitry communicates with the microprocessor and the remaining circuitry by means of the address/data bus 168. Telemetry system 162 may correspond to telemetry system 330 in FIG. 5 and, via antenna 110 transmits and receives information from the external programmer or monitor. Sensor 167may correspond to sensor 344 in FIG. 5 and it may be a physical activity sensor or other sensor as discussed above. The output of sensor 167 is passed through sensor processing circuitry 166 which may similarly correspond to sensor processing circuitry 342 in FIG. 5.

Figure 8:
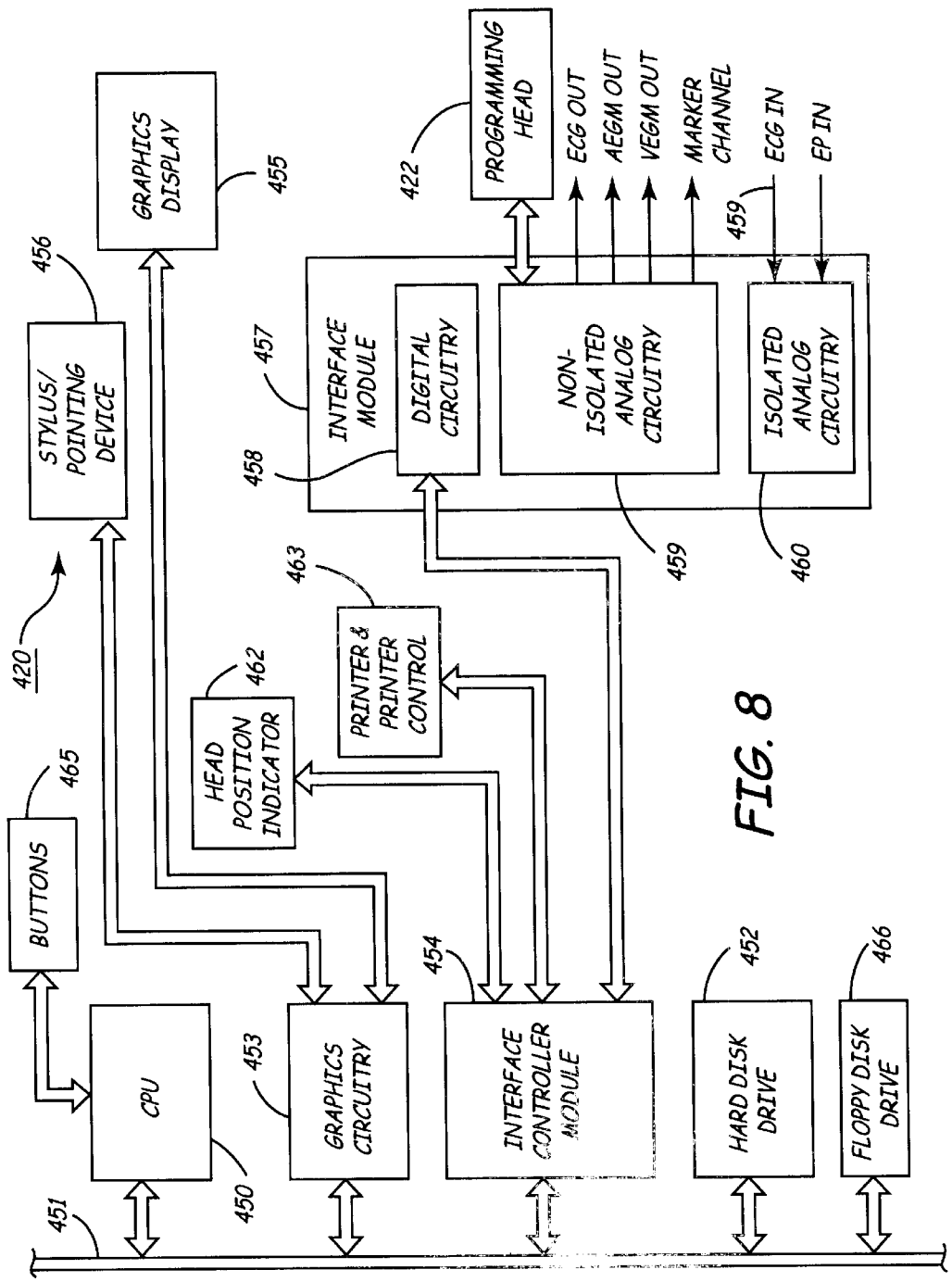
FIG. 8 is a functional schematic diagram of a programmer of a type useful in practicing the present invention.

FIG. 8 is a functional schematic of a programmer as illustrated in FIG. 4 appropriate for use in conjunction with the invention. Programmer 420 is a personal computer type, microprocessor-based device incorporating a central processing unit 450, which may be, for example, an Intel 80386 or 80486 or Pentium microprocessor or the like. A system bus 451 interconnects CPU 450 with a hard disk drive 452 storing operational programs and data and with a graphics circuit 453 and an interface controller module 454. A floppy disk drive 466 or a CD ROM drive is also coupled to bus 451 and is accessible via a disk insertion slot within the housing of the programmer 420. Programmer 420 further comprises an interface module 457, which includes digital circuit 458, non-isolated analog circuit 459, and isolated analog circuit 460. Digital circuit 448 enables interface module 457 to communicate with interface controller module 454. Information relating to monitored physiologic parameters, efficacy of delivered therapies and/or significant therapy related events may be stored in hard drive 452 or in RAM associated with microprocessor 450 and displayed on display 455. As discussed below such information may be stored in response to physician entry and/or in response to an uplink of the information from the associated implantable device. Graphics display 455 may also display real time data uplinked from the associated medical device or obtained from external sensors. Programmer 420 is also provided with a strip chart printer 463 or the like coupled to interface controller module 454 so that a hard copy of a patient's ECG, EGM, marker channel or of the graphics displayed on the display 455 can be generated.

In order for the physician or other caregiver or user to communicate with the programmer 420, control buttons 465 and/or optionally a keyboard coupled to CPU 50 is provided. The primary communication mode may also be by means of the graphics display screen 455 of the well-known "touch sensitive" type controlled by graphics circuit 453. A user of programmer 420 may interact therewith through the use of a stylus 456, also coupled to graphics circuit 453, which is used to point to various locations on screen 455, which display menu choices for selection by the user or an alphanumeric keyboard for entering text or numbers and other symbols.

As will be appreciated by those of ordinary skill in the art, it is often desirable to provide a means for programmer 20 to adapt its mode of operation depending upon the type or generation of implanted medical device to be programmed. Accordingly, it may be desirable to have an expansion cartridge containing EPROM's or the like for storing software programs to control programmer 420 to operate in a particular manner corresponding to a given type or generation of implantable medical device. In addition, in accordance with the present invention, it is desirable to provide the capability through the expansion cartridge or through the floppy disk drive 66 or CD ROM drive.

The non-isolated analog circuit 459 of interface module 457 is coupled to a programming head 422, which is used to establish the uplink and downlink telemetry links between the pacemaker 410 and programmer 420 as described above. Uplink telemetered EGM signals are received in programming head 422 and provided to nonisolated analog circuit 459. Non-isolated analog circuit 459, in turn, converts the digitized EGM signals to analog EGM signals and presents these signals on output lines A EGM OUT and V EGM OUT. These output lines may then be applied to a strip-chart recorder 463 to provide a hard-copy printout of the A EGM or V EGM for viewing by the physician. Similarly, the markers received by programming head 422 are presented on the MARKER CHANNEL output line from non-isolated analog circuit 459.

In order to ensure proper positioning of programming head 422 over the antenna of the associated implanted device, feedback is provided to the physician that the programming head 422 is in satisfactory communication with and is receiving sufficiently strong RF signals. This feedback may be provided, for example, by means of a head position indicator, e.g. a light-emitting diode (LED) or the like that is lighted to indicate a stable telemetry channel.

Isolated analog circuit 460 in interface module 547 is provided to receive external ECG and electrophysiologic (EP) stimulation pulse signals. In particular, analog circuit 460 receives ECG signals from patient skin electrodes 459 and processes these signals before providing them to the remainder of the programmer system in a manner well known in the art. Circuit 460 further operates to receive the EP stimulation pulses from an external EP stimulator for the purposes of non-invasive EP studies, as is also known in the art.

In conjunction with the above disclosed embodiments, it should be understood that in addition to being displayed by the programmer or monitor, according to the present invention, the stored information may also be employed to modify operational parameters of the implanted device. For example, in response to detected frequencies of tachyarrhythmias exceeding preset values, the microprocessors of the implanted cardioverter/defibrillators and pacemakers described above may activate an antiarrhythmia pacing prevention therapy or modify an antiarrhythmia pacing prevention therapy, activate or modify antiarrhythmia therapies, or the like. Similarly, the information collected according to the present invention may also be employed to trigger warning signals or alarms, to alert the patient that the physiologic parameters monitored indicate the necessity of medical intervention, or at least of a visit to the doctor. Further, it should be understood that the displays and data collection according to the present invention are intended to be programmable, that is, adjustable by the physician.

In preferred embodiments of the present invention, the physician, by means of the external programmer, will be able to select the specific types of information to be monitored, the resolution of the displayed information, the time scale along which the information is displayed, and the like. In preferred embodiments thus the invention provides a display mechanism that may be tailored by the physician to provide the particular information, in the particular format of most value in conjunction with monitoring and treating the patient in whom the implanted device is installed.

In conjunction with all embodiments of the present invention, it should also be understood that the external programmer or monitor associated with the implanted device may be located remotely from the implanted device. In such embodiments, the implanted device may communicate with the associated monitor directly over telephone lines as described in U.S. Pat. No. 5,433,736, issued to Nilsson, incorporated herein by reference in its entirety. Alternatively, the implanted device may communicate with a remote monitoring or programming device through an intermediary communication device, such as disclosed in U.S. Pat. No. 7,752,976, issued to Thompson; et al and incorporated herein by reference in its entirety. In such cases, communication may be by means of conventional phone lines, cellular phone, direct satellite communication or other communications link.

Figure 9:
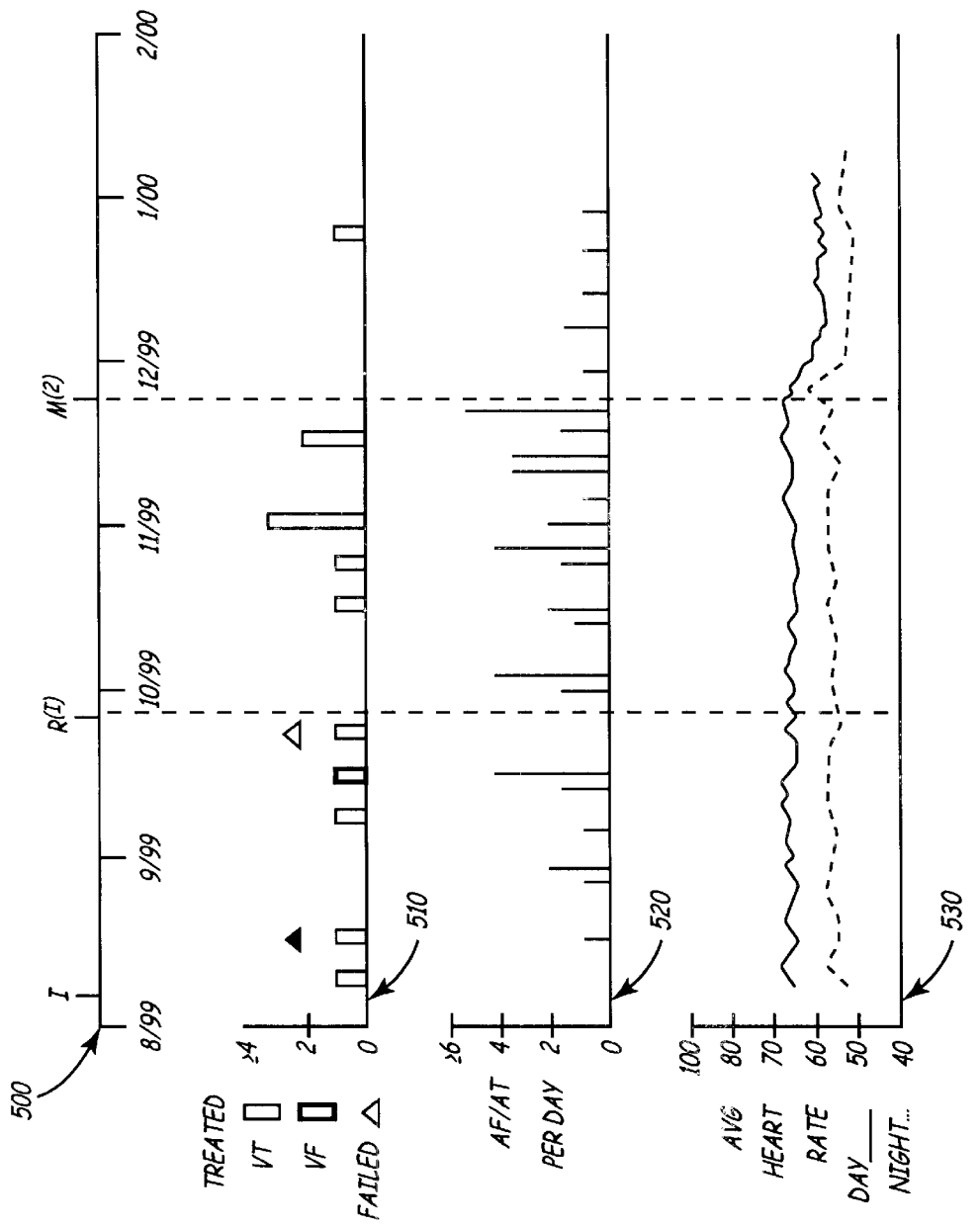
FIGS. 9, 10 and 11 are examples of the sorts of displays that may be provided according to the present invention.
Figure 10:
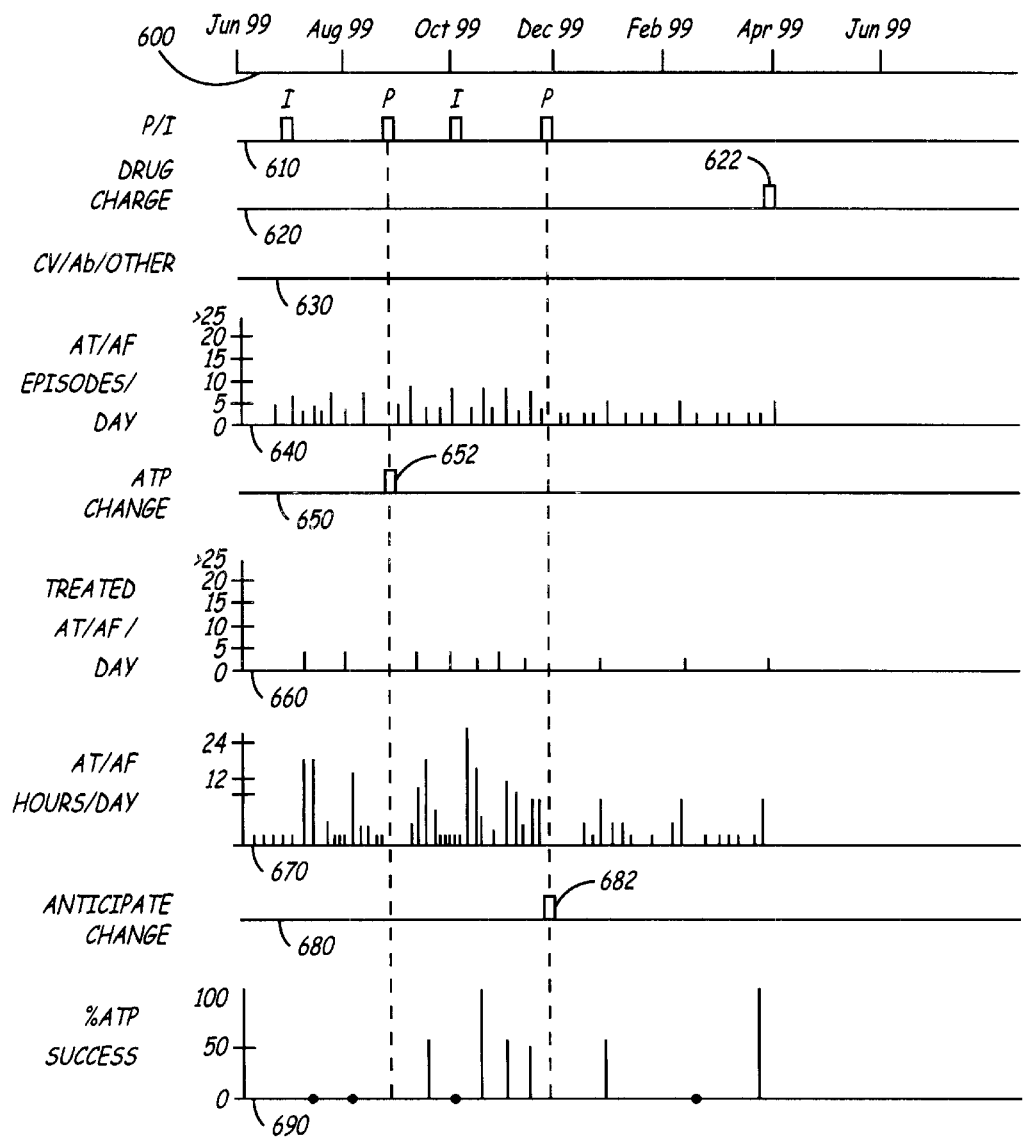
Figure 11:
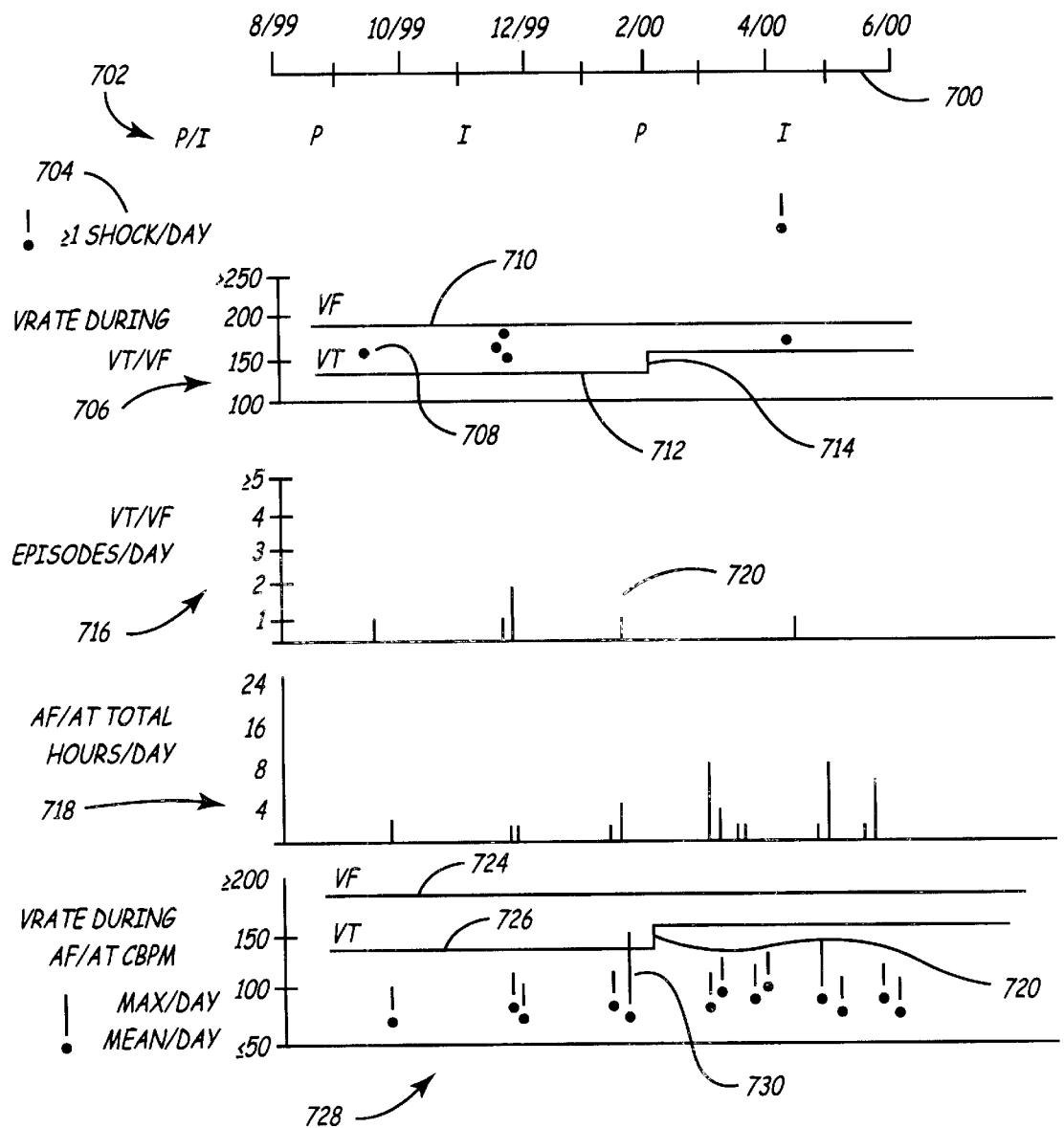

FIGS. 9, 10 and 11 are diagrams illustrating displays of time scaled data indicative of a patient's condition and the operational status of an implantable device, in conjunction with significant therapy related events.

FIG. 9 is an exemplary diagram of a display, which might be produced by a system according to the present invention. In particular, the display is of the type that might be produced in conjunction with an implanted pacemaker/cardioverter/defibrillator as generally illustrated in FIG. 5. The display would be shown on the graphics display of the external programmer or monitor (e.g. Graphics Display 455, FIG. 8) and/or on a paper print-out produced by printer 463 and would display information uplinked from the implanted device and/or stored on the hard disk (e.g. hard disk drive 452, FIG. 8) or in RAM associated with the CPU (e.g. 450, FIG. 8) of the external monitor or programmer. As discussed above, the information may be stored in its entirety in the RAM of the implanted device (e.g. RAM 266), and uplinked in its entirety to the external monitor or programmer, or may be stored by the external monitor or programmer and may comprise the results of multiple uplinks of information from the implanted device and/or keyboard entries by the physician indicative of therapy changes.

In FIG. 9, time line 500 sets forth the time scale for all of the information displayed. Above the time line are indications as to when the external programmer interrogated the implanted device at "I", as to when the external programmer reprogrammed some operational aspect of the implanted device at "R(1)" and as to the time of occurrence of a change in the patient's medication "M(2)". Trend line 510 illustrates occurrences of treated ventricular tachycardia (VT) and ventricular fibrillation (VF) over time, along with an indication as to the delivery of an unsuccessful therapy. It should be kept in mind that multiple therapies may be delivered in conjunction with a single detected tachyarrhythmia. The third time line 520 illustrates the number of hours in which the patient is in atrial fibrillation or atrial tachycardia per day, and the third time line 530 illustrates the patient's average day and night heart rates over a time period, as described in U.S. patent application No. 09/452,659, filed Dec. 1, 1998 by Padmanabhan, et al.

By comparing the times of occurrences of the therapeutically significant events, including the reprogramming at R(1) and the medication change at M(2), the physician may readily discern their effect on the patient's underlying condition. For example, at R(1), the delivered ventricular tachycardia therapies were adjusted, for example by selecting a different set of anti-tachycardia pacing therapies or by adjusting the coupling intervals for the initial scans of the anti-tachycardia patient therapies. As illustrated, following reprogramming of the delivered therapies, the number of unsuccessful therapies has decreased to zero, indicating that the programming change was successful in correctly adjusting the device to treat the patient's underlying ventricular tachyarrhythmias. At M(2), the increased dosage of the anti-arrhythmic drug taken by the patient can be seen to have resulted in a dramatic decrease in occurrences of atrial fibrillation, indicating that the drug regimen change was successful. The change in the drug regimen also can be seen to result in a substantial decrease in a patient's average day and night heart rate.

In FIG. 9 as illustrated, footnotes (1) and (2) are provided below the chart to indicate the specific nature of the therapeutic events. In simpler embodiments of the invention, the footnotes might be deleted, with changes in therapeutic events simply illustrated by letter code, e.g. R, M, etc. without specific explanation of the particular changes. Similarly, in more complex embodiments of the invention, a more detailed description of the therapeutic change may be provided, including for example, the specific details of the particular parameter changes associated with adjustment of the ventricular tachycardia therapy or the specifics of the increased dosage of the antiarrhythmic drug.

The diagram of FIG. 9 is merely exemplary of the sorts of displayed parameters that might be used in conjunction with an implanted anti-arrhythmia device, such as an implanted pacemaker/cardioverter/defibrillator. Additional or alternative displayed trend lines or time lines might include, for example, number of VTNVF episodes per day, occurrences of more than one delivered high voltage shock per day, ventricular rates during detected VTNF, non-sustained tachycardia episodes per day, ventricular rates during AF/AT, percent pacing per day in the atrium and ventricle, patient activity as described in the above-cited Stone et al application and heart rate variability as described in U.S. patent application Ser. No. 09/452,452,533, filed Dec. 1, 1999 by Padmanabhan et al. In preferred embodiments, the physician may be able to select from a library of available time line/ trend line displays for use in conjunction with the present invention, selecting those which the physician believes are most appropriate for monitoring the patient's underlying condition and his response to delivered therapies.

FIG. 10 is an example of a display according to an alternative embodiment of the present invention. In particular, the display illustrated is of the type that might be produced in conjunction with an implanted pacemaker as generally illustrated in FIG. 6, having atrial anti-tachyarrhythmia therapies and atrial arrhythmia prevention pacing therapies. In FIG. 10, time line 600 establishes the time scale for the trend line displays below. In this embodiment, therapeutically significant events are provided with separate individual time lines for different types of significant events. In this context, time line 610 illustrates programming and interrogations of the implanted device, time line 620 is indicative of occurrences of changes in the patient's drug regimen, time line 630 is indicative of occurrences of other significant sensed events, such as external cardioversion, ablation, or other surgical procedures, time line 650 is indicative of occurrences of changes in anti-tachycardia pacing therapies available, and time line 680 is indicative of changes in arrhythmia prevention pacing modalities available, such as those described in U.S. Pat. No. 5,814,085, issued to Hill, U.S. Pat. No. 4,941,471, issued to Mehra, or U.S. Pat. No. 5,893,882, issued to Peterson, et al., all incorporated herein by reference in their entireties.

In conjunction with the time lines indicative of significant therapeutic events, the display includes trend lines indicative of the patient's underlying condition and the patient's response to delivered therapies. Trend line 640 illustrates the number of AT/AF episodes per day, trend line 660 illustrates numbers of treated episodes of atrial tachycardia or atrial fibrillation per day, trend line 670 illustrates total hours of atrial tachycardia or atrial fibrillation per day and trend line 690 illustrates percentage of success of atrial anti-tachycardia pacing regimens. By comparing the timing of the illustrated significant therapeutic events to the trend lines indicative of the patient's condition and/or his response to delivered therapies, an evaluation of the significant therapeutic events can readily be obtained. For example, following the illustrated change in atrial anti-tachycardia pacing therapies at 652, an increase in the percentage of success of anti-tachycardia pacing therapies can clearly be seen in trend line 690. Similarly, following a change in the programmed parameters of atrial tachyarrhythmia prevention pacing regimens at 682, a decrease in the number of AT/AF episodes per day can be seen in trend line 640 and a decrease in the total number of AT/AF hours per day can be seen in trend line 670. Similarly, as time passes, changes in the patient's underlying condition and/or response to delivered therapy following an indicated change in drug therapy at 622 may also be discerned.

FIG. 11 illustrates an alternative display which might be produced in conjunction with an implantable pacemaker/cardioverter/defibrillator. In the display of FIG. 2, a time line 700 is provided, which serves as a time scale for all displays below. Programming/interrogation events are illustrated at 702 by the presence of the symbols "P" and "I", placed along the time scale. Also illustrated at 704 is a time based display illustrating days on which one or more high voltage shocks are given, by means of a symbol (!) placed relative to the time line 700. In FIG. 11, a display of measurements of ventricular rate during VT/VF is provided at 706, with individual measured rates illustrated by dots, e.g. 708. In this display the ventricular fibrillation detection rate 710 and ventricular tachycardia detection rate 712 employed by the device are also illustrated graphically. In this display, a therapeutically significant event in the form of an upward adjustment of the detection rate for ventricular tachycardia is displayed graphically at 714, allowing the physician to readily discern the relationship between the VT detection threshold and the detected ventricular rates during detected episodes of VTNVF. Display 716 illustrates the cumulative number of VT/VF episodes per day, and display 718 illustrates the cumulative number of hours of atrial fibrillation/atrial tachycardia detected per day. Display 728 illustrates ventricular rate during detected AF/AT, illustrating both the maximum rate and the mean rate for each day. In this display, the detection rate thresholds for VF (724) and VT (726) are also displayed in a manner similar to that displayed in display 706. At 730, it can be detected that the ventricular rate in the presence of atrial fibrillation has exceeded the ventricular tachycardia detection rate. This display occurrence, in conjunction with the displayed detection of ventricular tachycardia or fibrillation at 720, suggests the possibility that ventricular tachycardia may have been incorrectly detected at 720 as a result of a rapid ventricular rate induced by atrial fibrillation. The adjustment of the ventricular tachycardia detection rate at 732 in conjunction with the subsequent portions of display 728, indicate that the upward adjustment of the ventricular tachycardia detection threshold resulted in no ventricular rates during atrial fibrillation or tachycardia rising to the level which might erroneously be detected as ventricular tachycardia. In this display, like the displays of FIGS. 9 and 10 discussed above, the ability of the physician to easily correlate changes in therapy with subsequent measured physiologic parameters provides a mechanism for allowing the physician to more accurately tailor the operation of the implanted device to the particular patient in whom it is installed.

The display of FIGS. 9, 10 and 11 should be taken as exemplary of the sorts of types of information that might be displayed in conjunction with an atrial antitachycardia pacemaker, as discussed above. Additional parameters which might also be displayed might include, for example, total percentages of pacing per day in the atrium and ventricle, percentage of pacing employing atrial arrhythmia prevention or anti-arrhythmia pacing modalities as discussed above, average day and night heart rates, heart rate variability, occurrences of ventricular tachycardias, and patient activity level.

In conjunction with FIGS. 9, 10 and 11 it should also be understood that in the case in which the implanted device employs a physiologic transducer in addition to or as an alternative to a patient activity sensor, corresponding trend lines might also be displayed, illustrating the outputs of oxygen saturation sensors, intracardiac pressure sensors, respiration sensors, and the like, which may provide further useful clinical information. It should also be understood that in the event the implanted device includes an implanted drug dispenser, that changes in drug related therapy may in fact relate to reprogramming of the implanted device itself, as opposed to physician initiated changes in intravenous or oral drug therapies. As such, the embodiments illustrated above should be considered exemplary, rather than limiting, with regard to the claims that follow.

In conjunction with the above disclosure, we claim:

1. A system for correlating long-term changes in a patient's arrhythmias, with an ICD, the system comprising:
   means for correlating changes between different trends;
   means for integrating information stored in the ICD, relating to patient's disease status, into said different trends;
   means for isolating a single clinical measure over time;
   means for providing a quick history of the patient's disease status; and
   means for viewing a clinical trend between a start- date and end date extending over the long-term implemented in the system to cooperate with said means for correlating, said means for integrating, said means for isolating and said means for providing such that clinicians may review and identify an exact time of tachyarrhythmia occurrence correlative to the patient's symptoms.

2. The system of claim 1 wherein said means for correlating changes further includes means for comparing times of occurrences of therapeutically significant events.

3. The system of claim 1 wherein said means for isolating a single clinical measure includes means for selecting from a time line/trend line displays.

4. The system of claim 1 wherein said means for providing a quick history of the patient's disease status includes means for comparing the timing of significant therapeutic events to trend lines indicative of the patient's condition and/or response to delivered therapies.

5. The system of claim 1 wherein said means for viewing includes a programmer in data communications with the ICD.

6. A system for correlating long-term changes in a patient's arrhythmias, with an implantable device and associated external device, the system comprising:

the implantable device including:
    means for transmitting information to and receiving information from the external device;
    monitoring ineans for monitoring a physiologic parameter; and
    means for providing information regarding the measured physiological parameter to the telemetry means for communication to the external device; and wherein the external device including:
    means for receiving information from the implanted device and for transmitting information to the implanted device;
    means for receiving information indicative of occurrences of significant therapeutic events including information regarding changes in a drug therapy; and
    display means for combining information received from the implantable device related to the monitored physiologic parameter with the information of therapeutic significance and for displaying the combined information in a time-scaled display wherein the measured physiologic parameter is displayed along a common time scale with indications of occurrences of the significant therapy related events.

7. The system of claim 6 wherein said means for receiving information indicative of occurrences of significant therapies includes means for determining when interrogations, programming and drug changes occur.

8. The system of claim 6 wherein said occurrences of significant therapy related events include trend lines illustrating occurrences of treated VT and VF overtime, indication of unsuccessful therapy.

* * * * *